United States Patent [19]
Hill, Jr. et al.

[11] Patent Number: 5,198,871
[45] Date of Patent: Mar. 30, 1993

[54] LASER-INDUCED-FLUORESCENCE INSPECTION OF JET FUELS

[75] Inventors: Ralph H. Hill, Jr.; David W. Naegeli, both of San Antonio, Tex.

[73] Assignee: Southwest Research Institute, San Antonio, Tex.

[21] Appl. No.: 717,265

[22] Filed: Jun. 18, 1991

[51] Int. Cl.⁵ .............................. G01N 21/64
[52] U.S. Cl. .................. 356/318; 250/458.1; 250/459.1
[58] Field of Search ................ 356/317, 318; 250/458.1, 459.1, 461.1

[56] References Cited

U.S. PATENT DOCUMENTS

| | | | |
|---|---|---|---|
| 4,018,530 | 4/1977 | Hirschfield | 250/459.1 |
| 4,071,298 | 1/1978 | Falconer | 356/73 |
| 4,127,329 | 11/1978 | Chang et al. | 356/301 |
| 4,236,071 | 11/1980 | Chimenti | 250/253 |
| 4,290,433 | 9/1981 | Alfano | 128/665 |
| 4,461,573 | 7/1984 | Lucht et al. | 356/318 |
| 4,479,499 | 10/1984 | Alfano | 128/665 |
| 4,580,059 | 4/1986 | Wolbeis et al. | 250/459.1 |
| 4,642,526 | 2/1987 | Hopkins | 315/244 |
| 4,645,918 | 2/1987 | Tsuchiya et al. | 250/213 VT |
| 4,802,762 | 2/1989 | Hill, Jr. | 356/318 |
| 4,866,283 | 9/1989 | Hill, Jr. | 250/461.2 |
| 5,049,738 | 9/1991 | Gergely et al. | 250/459.1 X |

OTHER PUBLICATIONS

Popi et al., "Determination of Polycyclic Aromatic Hydrocarbons in White Petroleum Products", Analytical Chemistry, vol. 47, #12, Oct. 1975, pp. 1947–1950.

Primary Examiner—Vincent P. McGraw
Attorney, Agent, or Firm—Pravel, Gambrell, Hewitt, Kimball & Krieger

[57] ABSTRACT

An optical inspection system for using laser-induced luminescence to detect the quality of materials, such as fuel. The inspection system comprises an excitation means for illuminating a specimen to cause it to produce fluorescent radiation. The spectral representation of the fluorescence produced by the specimen is compared to a reference spectrum to obtain an indication of the physical characteristics of the specimen.

2 Claims, 2 Drawing Sheets

LASER-INDUCED-FLUORESCENCE INSPECTION OF JET FUELS

FIELD OF THE INVENTION

The present invention relates generally to the field of optical inspection of materials. More specifically, the present invention provides a method and apparatus for utilizing laser-induced-fluorescence techniques to determine the quality of jet fuels. The laser-induced-fluorescence techniques of the present invention can be used to detect the existence of gums and other deposits in quantity of jet fuel.

BACKGROUND

It is well known that fuel impurities can adversely affect the performance of jet engines. The mechanism of the formation of deposits from thermally stressed jet fuels is a complex process involving several consecutive reactions steps. In the most general case, deposits form as the result of a fuel oxidation, of which the first step in the mechanism is the formation of peroxides. The thermal decomposition of peroxides and the ensuing chain propagation reactions lead to the formation of several oxygenated compounds and free radical species. The free radicals react with dissolved oxygen in the fuel to form relatively stable alkylperoxyl radicals; because these less reactive radicals tend to build up in the fuel, they have a greater probability of recombining with each other to form species that have slightly more than twice the molecular weight of the average fuel molecule. These higher molecular weight species, commonly known as gums, which are relatively insoluble in the fuel, contain high concentrations of oxygen and other heteroatoms such as sulfur and nitrogen that may be present in the fuel.

It is generally believed that the insolubles/gums are the precursors to deposit formation. Since deposit formation depends on parameters other than chemistry such as the flow conditions, mass transport and surface activity, thermal stability of a fuel seems to be best indicated by the fuel's tendency to form gums. A temperature dependent global rate constant for the formation of gums could then become a defined fuel property for thermal stability and could be used for predicting the potential deposit formation in aircraft fuel systems at specified temperature and flow conditions.

To determine the global rate constant for the formation of insolubles in fuels, the rate of gum formation needs to be measured under controlled conditions, specifically, constant temperature. However, the actual measurement of the rate of formation of gums hinges upon the current capability to measure gum concentration in jet fuels. Currently, the ASTM D381 method using the stream jet evaporation technique is the only established method of measuring the concentration of gums in jet fuels. This analysis method involves a large sample size, lengthy analysis, and yields poor accuracy. Furthermore, its intrusiveness tend to discourage the use of the D381 method in an examination of the kinetics of gum formation in jet fuels.

The deposits that form in aircraft fuel systems include soft gums, strongly adhering lacquers, and varnishes. Sometimes there are very hard, brittle substances resembling coke. When deposits are formed by autooxidation of jet fuel, they have oxygen concentrations much greater than deposits from the thermally unstressed fuel, and their hydrogen-to-carbon ratio is lower than that of the original fuel. If the unstressed fuel contains hetroatoms such as sulfur and nitrogen, these relatively polar species are concentrated in the deposit.

There is very little quantitative data on the composition of fuel-system deposits formed from jet fuels. Furthermore, there is little data available on the compositions of gums formed by the autooxidation of fuels. The data on gums are important because they are precursors of deposit formation and thus provide an indication of deposit composition. Data pertaining to the compositions of gums formed by the autooxidation of heating oil and gasoline show that the polar components, including the hetroatoms oxygen, sulfur, and nitrogen, are highly concentrated in the gum, although they are usually present in only minute amounts ($<<1\%$) in the original fuel.

In view of the difficulties in measuring gums in jet fuels, spectroscopic methods of analysis have been explored. In the examination of fuels that contain gums, it has been found that the gums seem to always cause the fuel to have a slight brandy color that is characteristic of light absorption in the blue region of the visible spectrum. Other similar observations have been reported, such as the work by Bhan et al. reported in "Color Change/Sediment Formation in Marine Diesel Fuels, Task II," NIPER-B06710-2 (1986), which suggested a correlation between color change and sediment formation in marine diesel fuels.

The fact that pristine hydrocarbon fuels do not absorb light in the visible region of the spectrum, but gums have a finite absorption there, suggests that a spectroscopic method of measuring gums is possible. The first method that comes to mind is simply light absorption in the blue region (ca. 450 nm) of the spectrum as mentioned above. Although absorption would appear to work in principle, it does not appear to be strong enough to indicate that a highly sensitive method of measuring gums could be developed. A more sensitive method requires a laser diagnostic technique, such as that discussed hereinbelow.

SUMMARY OF THE INVENTION

The present invention provides a method of inspection and quality detection which can be used for analyzing fuel, particularly jet fuel having gums with a molecular composition which provides fluorescence characteristics. The fluorescent radiation from a desired quantity of fuel has a specific characteristic spectrum which can be compared to and differentiated from the spectrum radiated from an undesired quantity of fuel. Through the use of laser-induced luminescence, or more particularly laser-induced fluorscence, it is possible to detect minor differences in the characteristics of the fuel which might not be detected using standard detection techniques.

The invention inspection and sorting system comprises an excitation source which illuminates the fuel to be examined in order to cause that fuel to produce fluorescent radiation. In a preferred embodiment of the invention, the excitation source is a laser. A light detection means is operable to detect the fluoresent light produced by the fuel under examination and is operable to produce a spectral representation of the fluorescent light produced by the fuel. This spectral representation is processed in a processing means capable of differentiating between the spectrum (or portion of the spectrum) of a desired fuel and that of an undesired fuel.

The invention method for inspecting fuel comprises the steps of illuminating the fuel with light from an excitation source, thereby causing the fuel to fluoresce; detecting the fluorescent light reradiated by the fuel and producing an output signal in response thereto; processing the output signal to obtain a spectral representation of the reradiated light; and comparing the spectrum, or portion thereof, of the fuel under examination to the corresponding spectrum of a desired fuel.

DETAILED DESCRIPTION OF THE PREFERRED EMBODIMENT

Figure 1:
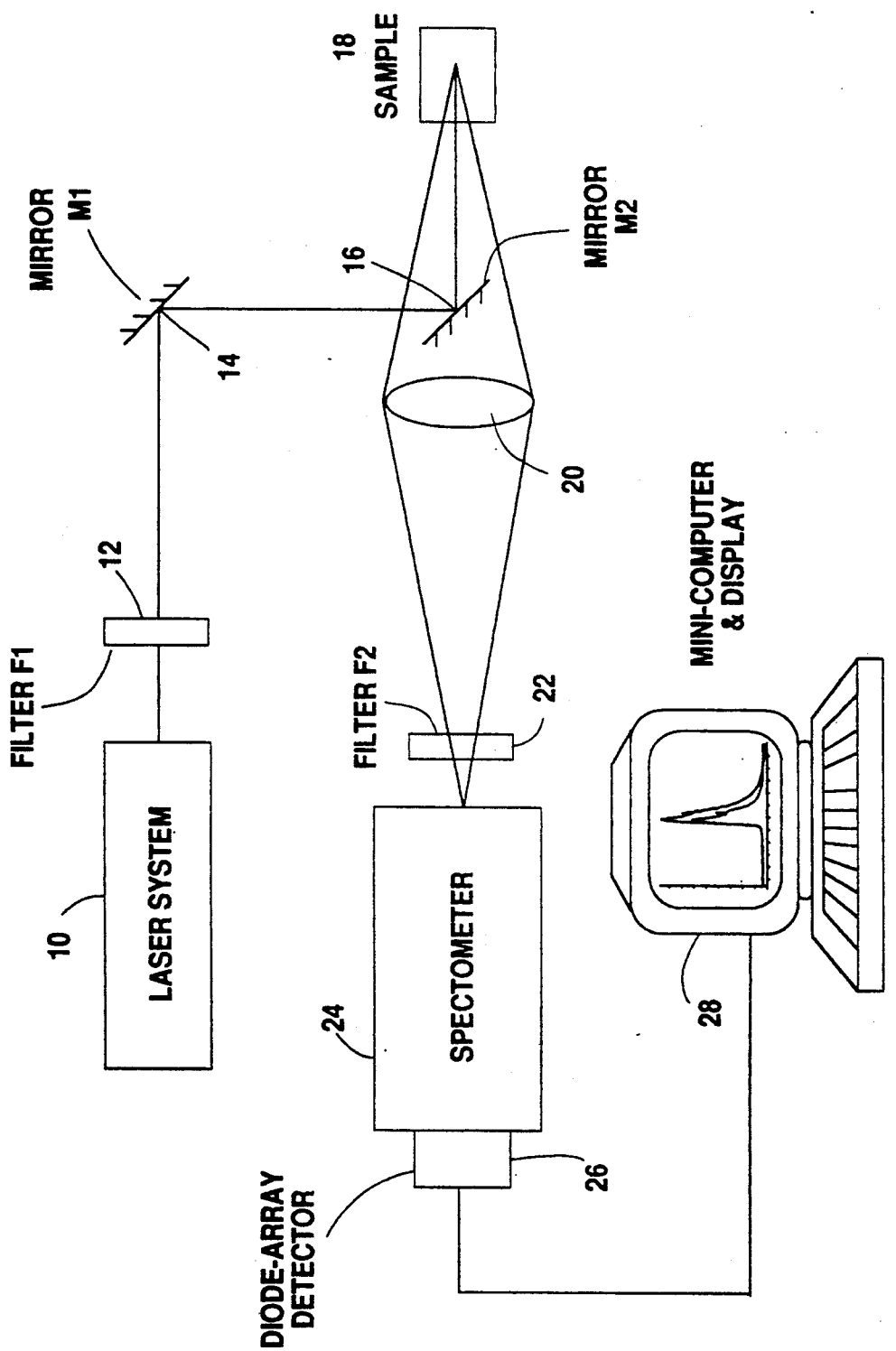
FIG. 1 is a schematic representation of the system configuration of the preferred embodiment used to determine the quality of a jet fuel sample using laser-induced-fluorescence techniques.

FIG. 1 is a schematic representation of the preferred embodiment of the invention system for optical inspection of a fuel product. Light from an excitation source 10 is passed through a filter 12 and reflected by mirrors 14 and 16 to illuminate a fuel sample 18 to be tested for fluorescence. In the preferred embodiment of the invention the excitation source 10 is a laser having a suitable wavelength to cause fluorescence. All subsequent discussion of the excitation source 10 will refer generally to a laser.

The fluorescence characteristics of the test sample 18 are determined by analysis of the light reradiated by the sample. The reradiated light passes through lens 20, filter 22 and is used as input for the spectrometer 24. The filter 22 can be selected to minimize the scattered light from the laser 10. The spectrometer 24 disperses the light which is then detected by the diode array detector 26 and amplified to provide input for a suitable display device 28, such as the minicomputer display 28 shown in FIG. 1.

In order to understand the principles of operation of the present invention, it is important to understand the meaning of luminescence, as well as the historical evolution of the definition of luminescence. Historically, materials were said to exhibit characteristics of "luminescence" if they emitted photons after being irradiated with light having a wavelength in the range of approximately 1800 to 3700 Angstroms (ultraviolet). Prior art definitions of this phenomenon have included two categories: fluorescence and phosphorescence. A material was said to exhibit fluorescence if the luminescence ceased after termination of the irradiation. However, if the luminescence persisted after irradiation, the phenomena was termed phosphorescence.

The above-mentioned definitions evolved at a time when observations of the persistence of luminescence were made with the unaided eye. The development of sophisticated instruments capable of measuring the persistence of luminescence for very short time periods, e.g., nanoseconds, has led to a more precise definition of the above-mentioned terms and has changed the definition of luminescence for some materials. For example, it is now known that many materials which have been characterized in the literature as being fluorescent emit luminescence for as long as 1000 microseconds after termination of excitation. This luminescence offers significant information regarding the physical characteristics of the illuminated material and in the present invention can be used to distinguish between desired fuel and fuel containing contaminants, as will be discussed in greater detail below.

It is well known that certain materials luminesce in the presence of ultraviolet or blue light and that the variation of the visible light luminescence can be used to determine certain features of the material. An example of an apparatus for using these phenomena to detect the presence of caries in human teeth is shown in U.S. Pat. Nos. 4,290,433 and 4,479,499 issued to Alfano. The luminescence in human teeth which is essential to the methods shown in these patents is dependent on the recognition of total visible luminescence. Further, the detection of the caries as shown therein relies on a visual recognition of differences in the color of the reradiated light from the teeth. While this luminescence technique is useful for detecting certain types of characteristics of materials, it is not suitable for an application such as that shown in the present invention because the technique is dependent on visual recognition of color differences in the luminescence of the material.

Quantitative measurements show that there is sometimes a very strong correlation between the laser-induced luminescence and physical characteristics of the material. Many times this is due to the fact that fluorescence reveals relationships between molecular functional groups, for instance conjugation. (This is in contrast to infrared absorption techniques, which are mainly used to reveal the presence of individual molecular functional groups.) Due to alteration of the relationships between certain molecular functional groups during degradation, laser-induced luminescence can be used to monitor degradation processes.

With the monochromaticity and power density available with lasers, transitions can be probed in molecules that are not normally thought of as fluorescent. For instance, chromophores that exhibit ultraviolet absorption can sometimes be induced to fluorescence with laser excitation in the visible region of the spectrum; representative examples include esters, ethers, and amines. This effect can be very important from the viewpoint of practical implementation.

One would not normally think of a fuel gum as a fluorescent material because, under standard room light conditions, the dominant process is simple light scattering and absorption. The wavelength dependence of these processes gives the fuel its characteristic color. Each photon of light is either absorbed or scattered by the fuel, but the wavelength remains essentially the same. Since room light contains all visible wavelengths, any fluorescence effects are completely masked to the unaided eye. The desired fluorescent effects can be observed, however, by illuminating the fuel with laser light at an appropriate wavelength, e.g., 488 nm, and looking at it through a filter that only passes longer wavelengths.

For a given excitation spectrum, samples of a material can have different fluorescence or phosphorescence spectra, even though they appear visually similar. The method and apparatus of the present invention differs from standard ultraviolet fluorescence techniques in that it takes advantage of the complicated excitation-luminescence spectra of the gums. The present invention is based on the discovery that fuel and gums have distinctive characteristic responses to radiation at certain frequencies. In particular, these characteristic responses can be used to differentiate between various grades of fuel and can also be used to differentiate between desired fuel and fuel which is contaminated with gums.

The invention method overcomes the shortcomings of previous optical inspection systems because it takes advantage of complex excitation-luminescence spectra of jet fuels. Thus, two quantities of jet fuel which both absorb approximately the same spectrum can have different fluorescence characteristics which can be distinguished to differentiate between desired fuel and fuel containing contaminants.

In the preferred embodiment of the present invention, the excitation source 10 and detector 24 may implemented using a Turner model 430 spectrofluorometer with a xenon lamp light source. Alternatively, the laser 10 may be implemented using Argon Ion laser source at 488 nm. The filter 22 may be implemented using a Schott-glass OG530 blocking filter, and in the preferred embodiment, scattered laser light, except for that at 488 nm, is removed by the filter. The system of the present invention could be implemented using fiber optics, known in the art. In addition the spectrometer used for the detector 24 could be replaced with a simple filter and photomultiplier tube system with appropriate supporting electronics.

Experimental results from embodiments using a Turner model 430 spectrofluorometer showed that there was a distinct, but very weak, fluorescence at about 550 nm from a solution of acetonitrile containing about 80 mg/dL of gum. The fluorescence was most intense when the incident xenon lamp light source was blue (ca. 450 nm). However, when an Argon Ion laser source at 488 nm was used as the incident light source 10, the fluorescence was considerably stronger since the laser light source was several orders of magnitude more intense at 488 nm than the xenon lamp light source.

Figure 2:
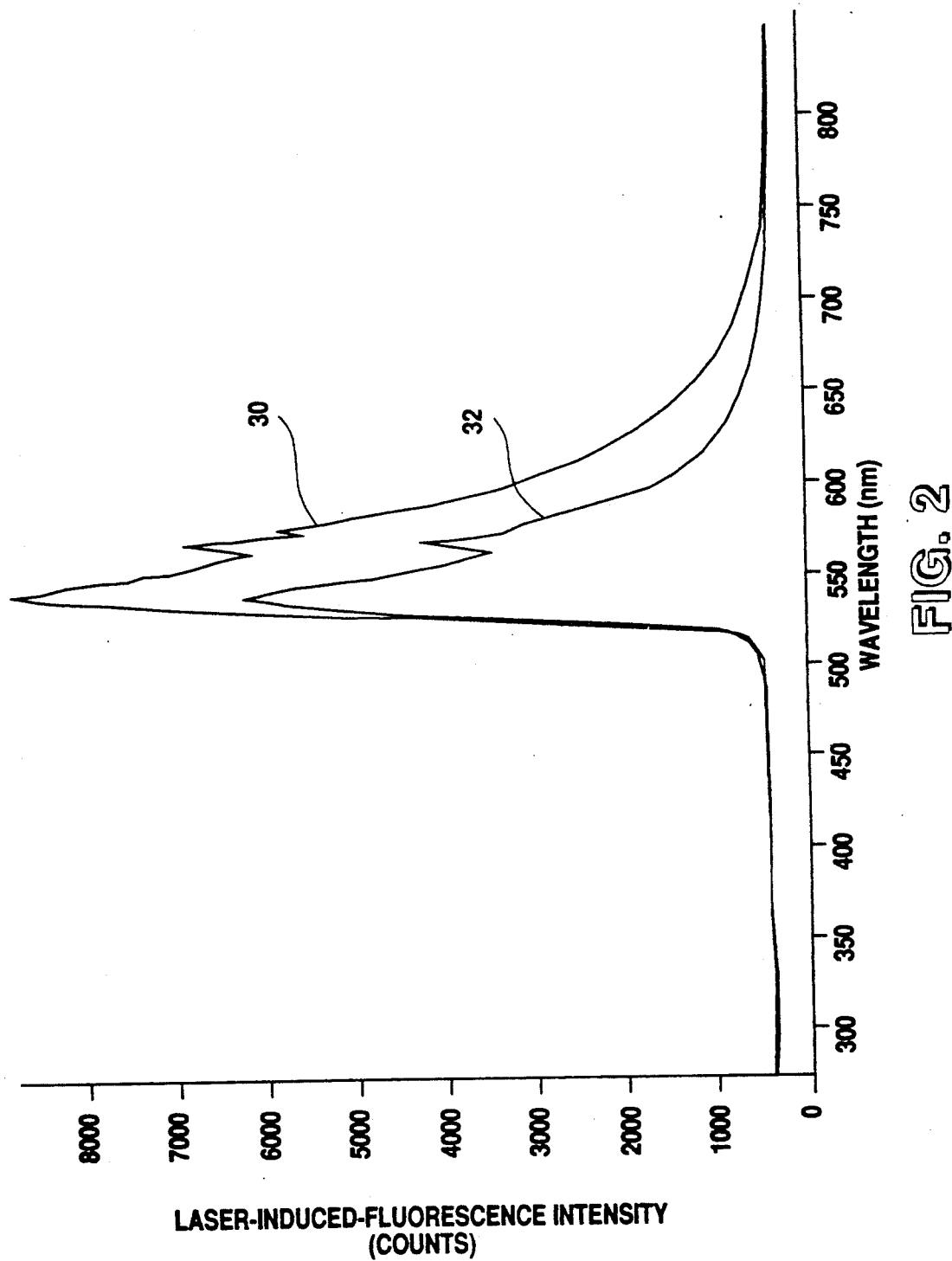
FIG. 2 is a graphical representations of fluorescence amplitude of a sample of fuel as a function of wavelength.

A typical output displayed using the invention system is shown in FIG. 2. The upper curve 30 represents the spectrum observed for gum in the jet fuel, while the lower curve 32 represents the spectrum observed for a neat, or pure, fuel sample. Alternatively, the signals produced by the system could be modified such that the upper curve could represent the desired material, while the lower curve could represent the fuel to be discarded. The main requirement is that there must be difference between the observed spectra of the materials.

In some cases, additives may be used to enhance the effect of the laser-induced-fluorescence. Additionally, treatment of some fuels may be necessary to give very precise results, such as degassing of excess free oxygen (in some fuels).

While the method and apparatus of the present invention have been described in connection with the preferred embodiment, it is not intended to limit the invention to the specific form set forth herein, but on the contrary, it is intended to cover such alternatives, modifications, and equivalents as may be included within the spirit and scope of the invention as defined by the appended claims.

What is claimed is:

1. An optical system for inspecting a sample of fuel to determine the existence of contaminants, such as gums, in said sample, comprising:

a laser for illuminating said sample with a quantity of laser light, said laser producing light having a wavelength of approximately 488 nanometers, for causing fuel in said sample to produce fluorescent radiation;

means for detecting said fluorescent radiation and for producing an output data signal in response thereto; and means for correlating said output data signal with the existence of contaminants, such as gums, in said sample of fuel.

2. A method for identifying contaminants, such as gums, in a sample fuel, comprising the steps of:

exciting said sample of fuel with a source of laser light having a wavelength of approximately 488 nanometers, causing said sample of fuel to produce fluorescent radiation;

detecting fluorescent radiation produced by said sample; and correlating said detected fluorescent radiation with the existence of contaminants, such as gums in said sample of fuel.

* * * * *